(12) United States Patent
Kulesa et al.

(10) Patent No.: US 8,308,723 B2
(45) Date of Patent: Nov. 13, 2012

(54) TISSUE-PENETRATING GUIDEWIRES WITH SHAPED TIPS, AND ASSOCIATED SYSTEMS AND METHODS

(75) Inventors: Larry B. Kulesa, Bothell, WA (US); David C. Auth, Kirkland, WA (US); Ryan E. Kaveckis, Everett, WA (US)

(73) Assignee: CoAptus Medical Corporation, Redmond, WA (US)

( * ) Notice: Subject to any disclaimer, the term of this patent is extended or adjusted under 35 U.S.C. 154(b) by 613 days.

(21) Appl. No.: 12/576,928

(22) Filed: Oct. 9, 2009

(65) Prior Publication Data
US 2011/0087211 A1 Apr. 14, 2011

(51) Int. Cl.
*A61B 18/14* (2006.01)

(52) U.S. Cl. .......................................... 606/41

(58) Field of Classification Search ............... 606/27, 606/34, 41, 129; 600/585
See application file for complete search history.

(56) References Cited

U.S. PATENT DOCUMENTS

| | | | |
|---|---|---|---|
| 4,273,127 A | 6/1981 | Auth et al. | |
| 4,682,596 A | 7/1987 | Bales et al. | |
| 4,998,933 A | 3/1991 | Eggers et al. | |
| 5,242,441 A * | 9/1993 | Avitall | 606/41 |
| 5,336,252 A | 8/1994 | Cohen | |
| 5,364,393 A | 11/1994 | Auth et al. | |
| 5,383,917 A | 1/1995 | Desai et al. | |
| 5,403,311 A | 4/1995 | Abele et al. | |
| 5,490,837 A | 2/1996 | Blaeser et al. | |
| 5,507,744 A | 4/1996 | Tay et al. | |
| 5,522,873 A | 6/1996 | Jackman et al. | |
| 5,584,872 A | 12/1996 | LaFontaine et al. | |
| 5,709,224 A | 1/1998 | Behl et al. | |
| 5,782,848 A | 7/1998 | Lennox | |
| 5,782,899 A | 7/1998 | Imran | |
| 5,824,055 A | 10/1998 | Spiridigliozzi et al. | |
| 5,827,268 A | 10/1998 | Laufer | |
| 6,030,380 A | 2/2000 | Auth et al. | |
| 6,235,021 B1 | 5/2001 | Sieben | |
| 6,565,562 B1 | 5/2003 | Shah et al. | |
| 6,699,245 B2 | 3/2004 | Dinger et al. | |

(Continued)

FOREIGN PATENT DOCUMENTS
WO  WO-0113810  3/2001
(Continued)

OTHER PUBLICATIONS

U.S. Appl. No. 12/246,349, filed Oct. 6, 2008, Herrin.

*Primary Examiner* — Michael Peffley
*Assistant Examiner* — Daniel Fowler
(74) *Attorney, Agent, or Firm* — Perkins Coie LLP

(57) ABSTRACT

Tissue-penetrating guidewires with shaped tips, and associated systems and methods are disclosed. A patient treatment system in accordance with one embodiment of the disclosure includes a tissue-penetrating guidewire that in turn includes a flexible segment having a distal portion and a proximal portion. The flexible segment is elongated along an elongation axis. A penetrating member is positioned at the distal portion and includes at least one blade segment having a tapered outer peripheral surface and an adjacent generally sharp edge. The blade segment extends to a distal end of the penetrating member to form a generally blunt tip. In operation, the guidewire can be connected to an electrical current source to deliver high frequency current to the penetrating member.

32 Claims, 10 Drawing Sheets

U.S. PATENT DOCUMENTS

| | | |
|---|---|---|
| 6,709,440 B2 | 3/2004 | Callol et al. |
| 6,939,348 B2 | 9/2005 | Malecki et al. |
| 7,166,104 B2 * | 1/2007 | Young et al. .................... 606/41 |
| 7,257,450 B2 | 8/2007 | Auth et al. |
| 7,270,662 B2 | 9/2007 | Visram et al. |
| 7,473,252 B2 | 1/2009 | Barry |
| 8,021,359 B2 | 9/2011 | Auth et al. |
| 2003/0069570 A1 | 4/2003 | Witzel et al. |
| 2004/0092973 A1 | 5/2004 | Chanduszko et al. |
| 2004/0153057 A1 | 8/2004 | Davison |
| 2004/0153098 A1 | 8/2004 | Chin et al. |
| 2004/0187875 A1 | 9/2004 | He et al. |
| 2004/0243122 A1 | 12/2004 | Auth et al. |
| 2005/0033288 A1 | 2/2005 | Eggers et al. |
| 2005/0119675 A1 | 6/2005 | Adams et al. |
| 2006/0052821 A1 | 3/2006 | Abbott et al. |
| 2006/0200197 A1 | 9/2006 | Brenzel et al. |
| 2007/0021739 A1 | 1/2007 | Weber |
| 2007/0043318 A1 | 2/2007 | Sogard et al. |
| 2007/0060858 A1 | 3/2007 | Sogard et al. |
| 2007/0203479 A1 | 8/2007 | Auth et al. |
| 2008/0009859 A1 | 1/2008 | Auth et al. |
| 2008/0140064 A1 | 6/2008 | Vegesna |
| 2008/0221482 A1 * | 9/2008 | Mondry et al. ................ 600/585 |
| 2009/0005780 A1 | 1/2009 | Kato |
| 2009/0069809 A1 | 3/2009 | Ootsubo |
| 2009/0093802 A1 | 4/2009 | Kulesa et al. |
| 2009/0093803 A1 | 4/2009 | Herrin |
| 2009/0118726 A1 | 5/2009 | Auth et al. |
| 2009/0131925 A1 | 5/2009 | Tempel et al. |
| 2011/0087211 A1 | 4/2011 | Kulesa et al. |
| 2011/0218503 A1 | 9/2011 | Kaveckis et al. |

FOREIGN PATENT DOCUMENTS

| | | |
|---|---|---|
| WO | WO-2005046487 A1 | 5/2005 |
| WO | WO-2005115256 | 12/2005 |
| WO | WO-2008079826 A2 | 7/2008 |
| WO | WO-2008/137649 A2 | 11/2008 |

* cited by examiner

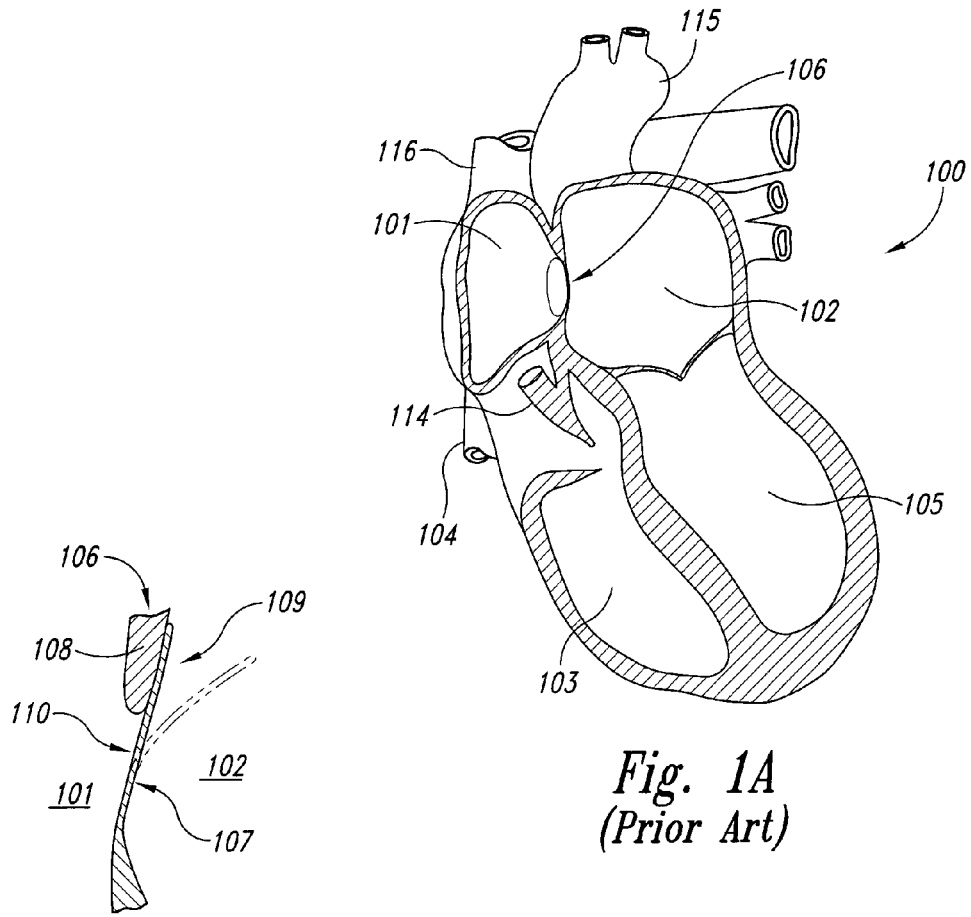
Fig. 1A
(Prior Art)
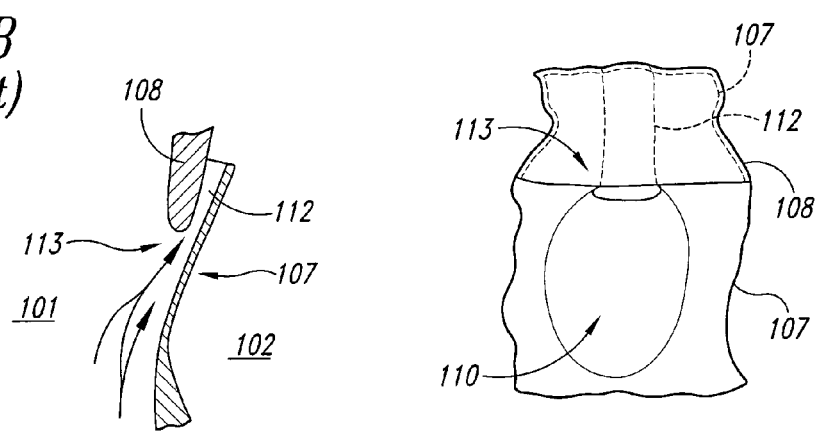
Fig. 1B
(Prior Art)
Fig. 1C
(Prior Art)
Fig. 1D
(Prior Art)

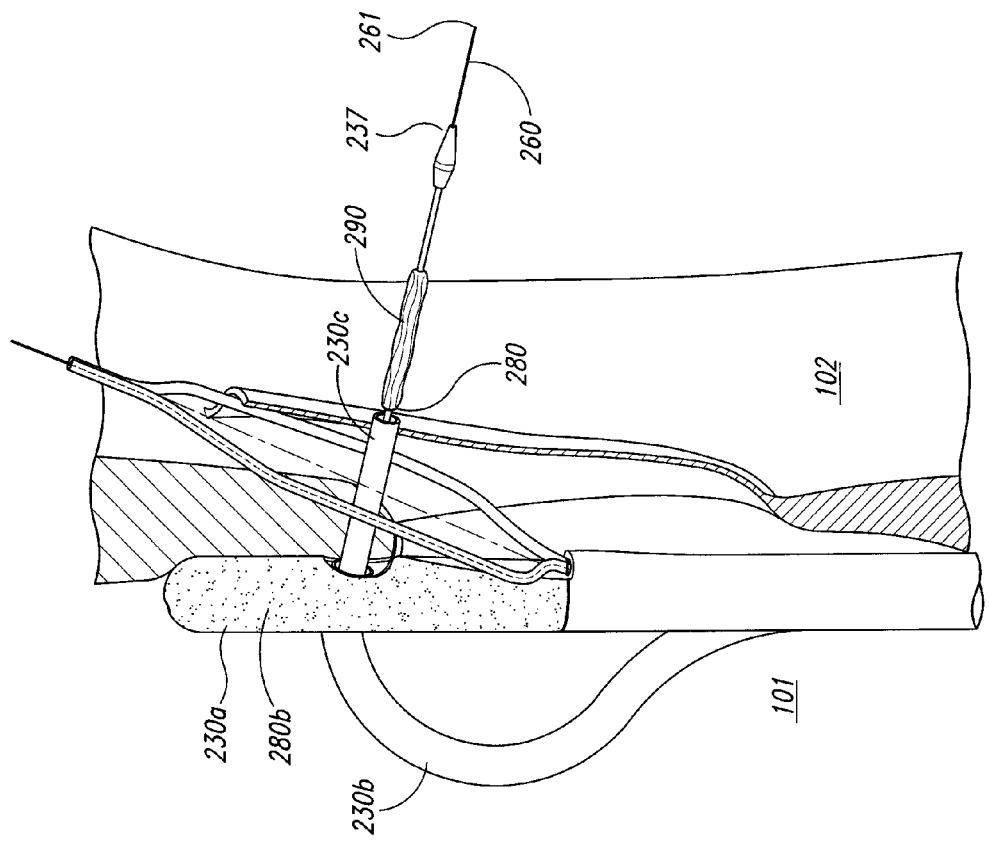
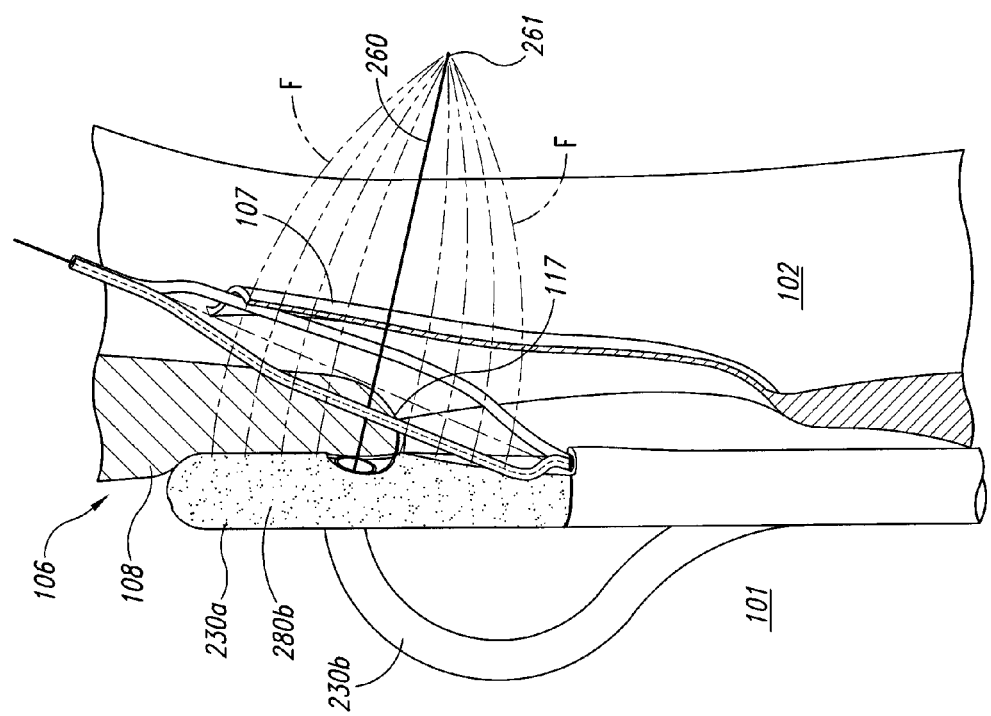
Fig. 3E
Fig. 3F

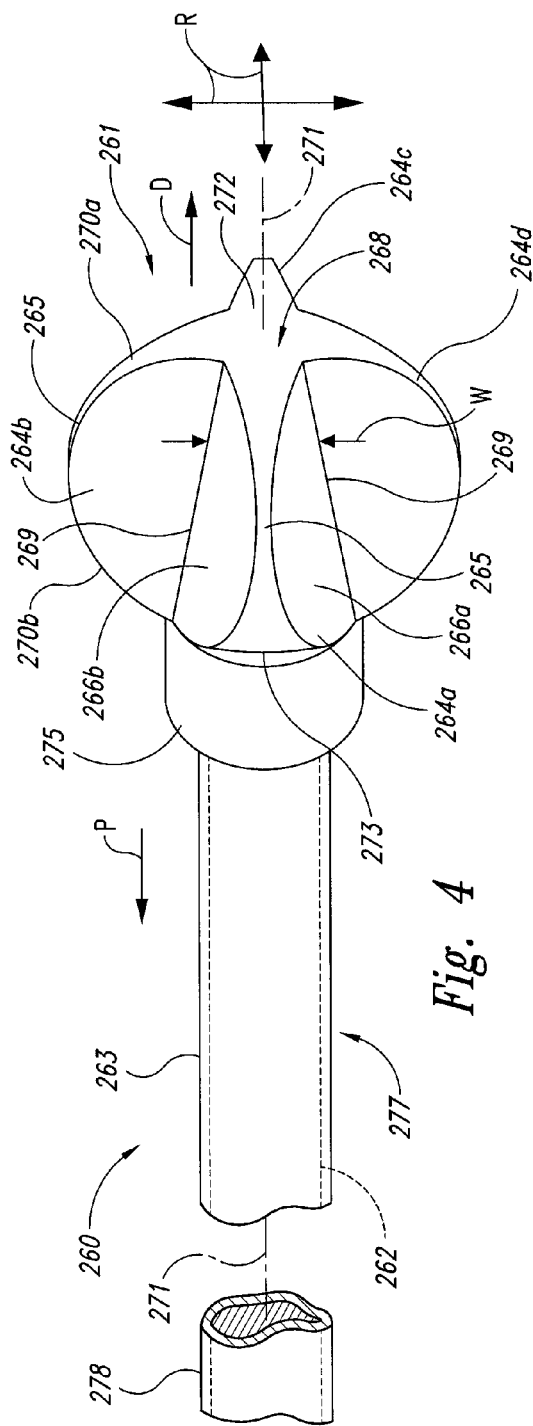
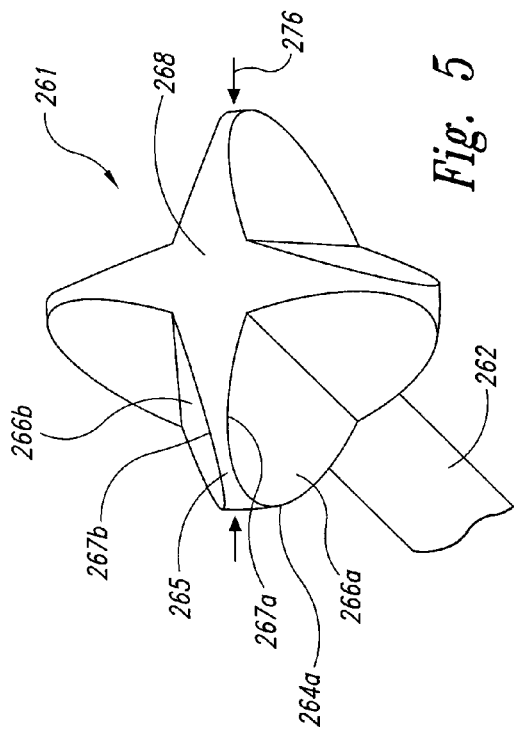

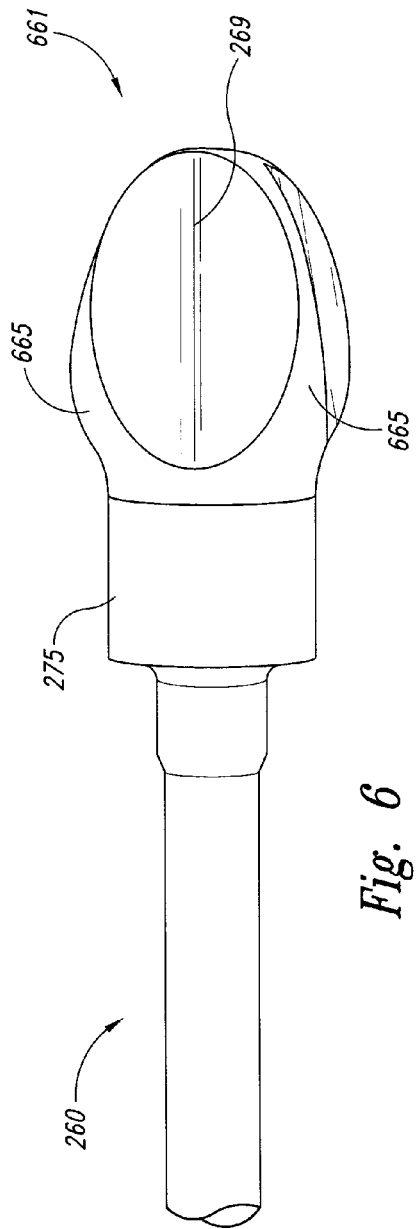
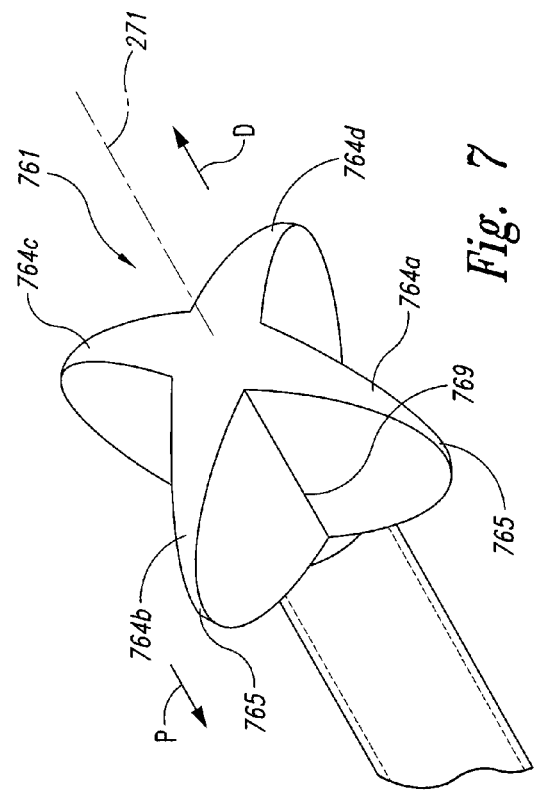

TISSUE-PENETRATING GUIDEWIRES WITH SHAPED TIPS, AND ASSOCIATED SYSTEMS AND METHODS

TECHNICAL FIELD

The present disclosure is directed generally to tissue-penetrating guidewires with shaped tips, and associated systems and methods.

BACKGROUND

The human heart is a complex organ that requires reliable, fluid-tight seals to prevent de-oxygenated blood and other constituents received from the body's tissues from mixing with re-oxygenated blood delivered to the body's tissues. FIG. 1A illustrates a human heart 100 having a right atrium 101, which receives the de-oxygenated blood from the superior vena cava 116 and the inferior vena cava 104. The de-oxygenated blood passes to the right ventricle 103, which pumps the de-oxygenated blood to the lungs via the pulmonary artery 114. Re-oxygenated blood returns from the lungs to the left atrium 102 and is pumped into the left ventricle 105. From the left ventricle 105, the re-oxygenated blood is pumped throughout the body via the aorta 115.

The right atrium 101 and the left atrium 102 are separated by an interatrial septum 106. As shown in FIG. 1B, the interatrial septum 106 includes a primum 107 and a secundum 108. Prior to birth, the primum 107 and the secundum 108 are separated to form an opening (the foramen ovale 109) that allows blood to flow from the right atrium 101 to the left atrium 102 while the fetus receives oxygenated blood from the mother. After birth, the primum 107 normally seals against the secundum 108 and forms an oval-shaped depression, i.e., a fossa ovalis 110.

In some infants, the primum 107 never completely seals with the secundum 108, as shown in cross-sectional view in FIG. 1C and in a left side view in FIG. 1D. In these instances, a patency often having the shape of a tunnel 112 forms between the primum 107 and the secundum 108. This patency is typically referred to as a patent foramen ovale or PFO 113. In most circumstances, the PFO 113 will remain functionally closed and blood will not tend to flow through the PFO 113, due to the normally higher pressures in the left atrium 102 that secure the primum 107 against the secundum 108. Nevertheless, during physical exertion or other instances when pressures are greater in the right atrium 101 than in the left atrium 102, blood can inappropriately pass directly from the right atrium 101 to the left atrium 102 and can carry with it clots, gas bubbles, or other vaso-active substances. Such constituents in the atrial system can pose serious health risks including hemodynamic problems, cryptogenic strokes, venous-to-atrial gas embolisms, migraines, and in some cases even death.

Traditionally, open chest surgery was required to suture or ligate a PFO 113. However, these procedures carry high attendant risks, such as postoperative infection, long patient recovery, and significant patient discomfort and trauma. Accordingly, less invasive techniques have been developed. Most such techniques include using transcatheter implantation of various mechanical devices to close the PFO 113. Such devices include the Cardia® PFO Closure Device, Amplatzer® PFO Occluder, and CardioSEAL® Septal Occlusion Device. One potential drawback with these devices is that they may not be well suited for the long, tunnel-like shape of the PFO 113. As a result, the implanted mechanical devices may become deformed or distorted and in some cases may fail, migrate, or even dislodge. Furthermore, these devices can irritate the cardiac tissue at or near the implantation site, which in turn can potentially cause thromboembolic events, palpitations, and arrhythmias. Other reported complications include weakening, erosion, and tearing of the cardiac tissues around the implanted devices.

Another potential drawback with the implanted mechanical devices described above is that, in order to be completely effective, the tissue around the devices must endothelize once the devices are implanted. The endothelization process can be gradual and can accordingly take several months or more to occur. Accordingly, the foregoing techniques do not immediately solve the problems caused by the PFO 113.

Still another drawback associated with the foregoing techniques is that they can be technically complicated and cumbersome. Accordingly, the techniques may require multiple attempts before the mechanical device is appropriately positioned and implanted. As a result, implanting these devices may require long procedure times during which the patient must be kept under conscious sedation, which can pose further risks to the patient.

BRIEF DESCRIPTION OF THE DRAWINGS

FIGS. 1A-1D illustrate a human heart having a patent foramen ovale (PFO) in accordance with the prior art.

FIGS. 3A-3I illustrate a process for closing a PFO in accordance with an embodiment of the disclosure.

FIG. 4 is a partially schematic, isometric illustration of a guidewire having a penetrating member configured in accordance with an embodiment of the disclosure.

FIG. 5 is a partially schematic, isometric illustration of a distal portion of the penetrating member shown in FIG. 4.

FIG. 6 is a partially schematic, side view of the distal region of the guidewire shown in FIGS. 4 and 5.

FIG. 7 is a partially schematic, isometric illustration of a guidewire having a penetrating member configured in accordance with another embodiment of the disclosure.

DETAILED DESCRIPTION

A. Introduction

Aspects of the present disclosure are directed generally to tissue-penetrating guidewires with shaped tips, and associated systems methods. Much of the discussion below is provided in the context of sealing patent foremen ovales (PFOs). However, in other embodiments, these systems and techniques may be used to treat and/or support treatment of other types of cardiac tissue and/or other tissue defects. For purposes of organization and ease of understanding, the following discussion is arranged in three sections. The present Section A provides a general introduction, Section B describes overall techniques and tissue sealing devices for sealing a patient's PFO, and Section C describes particular systems and techniques for penetrating the patient's septal tissue (e.g., the primum and/or secundum).

Several details describing devices or processes that are well-known to those of ordinary skill in the relevant art and often associated with such devices and processes are not set forth in the following description to avoid obscuring more significant aspects of the disclosure. Those of ordinary skill in the relevant art will understand that further embodiments may include features not disclosed in the following sections, and/ or may eliminate some of the features described below with reference to FIGS. 2-9.

Several of the techniques and associated devices described below include advancing a catheter into the right atrium of the patient's heart, piercing the septum between the right atrium and the left atrium, and placing an electrode or other energy transmitter in the left atrium. The energy transmitter applies energy to the septum to seal the PFO, optionally with the assistance of a balloon or other inflatable member, and is then drawn back through the septum. The catheter can then be withdrawn from the patient's body, leaving no foreign objects behind. A residual hole in the septum remaining after the electrode is withdrawn from the left atrium to the right atrium is expected to close over a short period of time as a result of the body's natural healing response.

Figure 2:
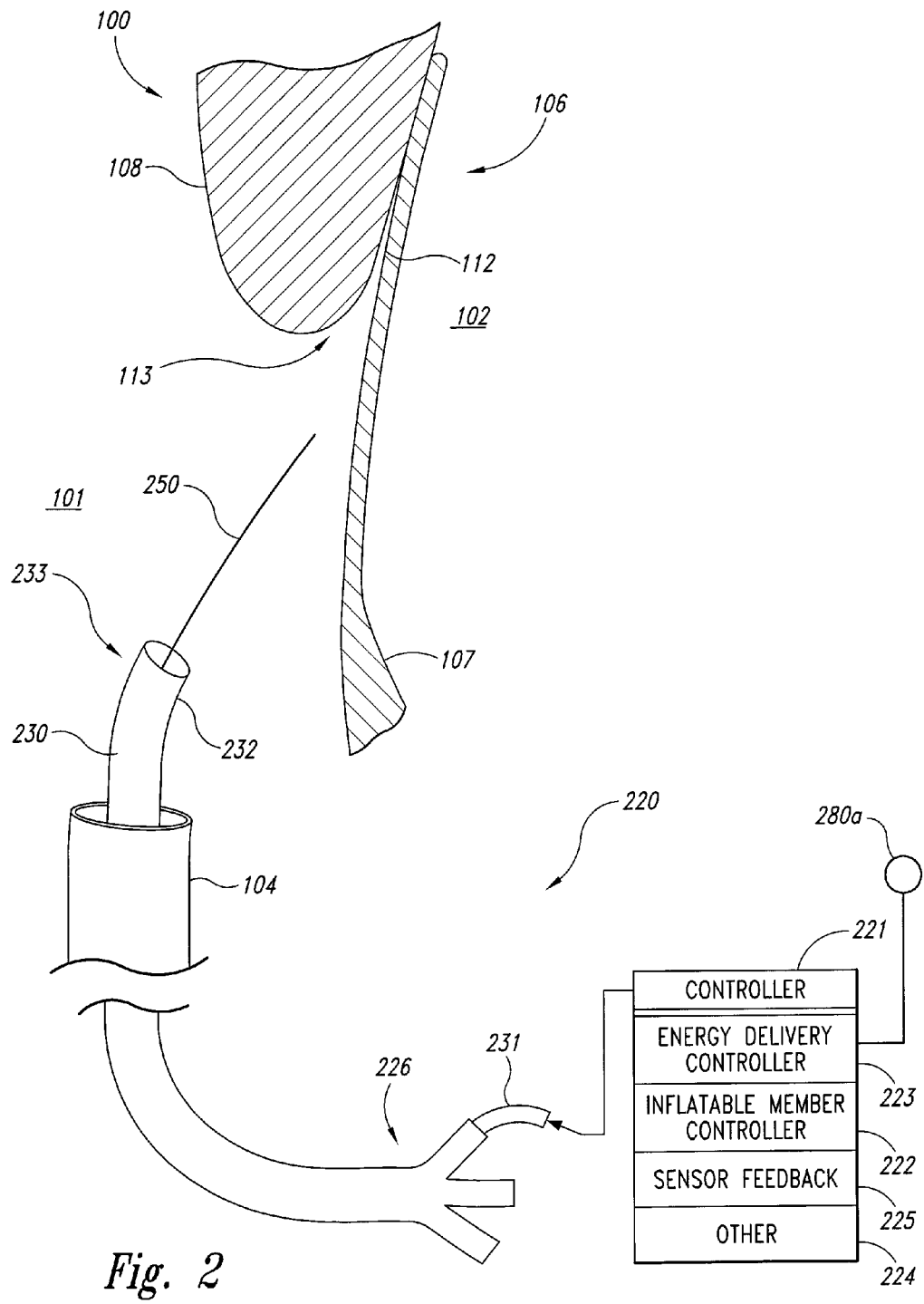
FIG. 2 illustrates a catheter positioned proximate to a PFO for treatment in accordance with several embodiments of the disclosure.

FIG. 2 is a schematic, not-to-scale illustration of the general components of a system 220 used to treat a patient in accordance with several embodiments of the disclosure. The system 220 generally includes one or more patient treatment devices, a term which, as used herein, includes devices that provide direct therapeutic benefits, and/or associated functions, including but not limited to, diagnostic functions, feedback functions, positioning functions and/or other support functions. The system 220 can include one or more guidewires 250 that are directed into the patient via an introducer 226, and are then threaded through the patient's vascular system to the heart 100. In the illustrated embodiment, the guidewire 250 enters the right atrium 101 from the inferior vena cava 104, and in other embodiments, the guidewire 250 can enter the right atrium 101 or other heart chamber from other vessels. One or more guidewires may also pass into the left atrium 102. One or more catheters 230 are then threaded along the guidewire 250 via corresponding lumens to treat a PFO 113 (e.g., the PFO tunnel 112) located between the primum 107 and the secundum 108 of the patient's septum 106. The catheter lumen(s) can be flushed with saline or another appropriate biocompatible fluid, either continuously or at selected intervals, to prevent clot formation, to lubricate the relative motion between the catheter(s) and devices within the lumens, to prime the lumens, and/or to purge the lumens of air bubbles.

The catheter 230 typically includes a distal end 232 within the patient's body, a working portion 233 toward the distal end 232, and a proximal end 231 that extends outside the patient's body. A controller 221 controls the functions carried out by the catheter 230 and the rest of the system 220, and can include an energy delivery controller 223 to control RF or other energy transmitted to the patient, an inflatable member controller 222 to control the operation of one or more inflatable members in the patient, a sensor feedback unit 225 to receive diagnostic information, and other controllers 224 to control other functions, for example, the motion of various guidewires and/or other elements of the system 220, and/or fluid delivery to elements of the system 220. A representative handheld controller configured for such purposes is described in co-pending U.S. application Ser. No. 12/246,349 filed on Oct. 6, 2008 and incorporated herein by reference. When the energy transmitter or delivery device includes an electrode, it may be operated in a monopolar manner, in which case a return electrode 280a is located remotely from the PFO 113. For example, the return electrode 280a can include a patient pad located at the back of the patient's left shoulder. In other embodiments, the electrode can operate in a bipolar manner, in which case the return electrode is generally located at or close to the PFO 113.

B. General Techniques and Systems For Treating a PFO

FIGS. 3A-3I are enlarged cross-sectional views of the heart regions around a PFO, and illustrate representative techniques and associated devices for sealing the PFO in accordance with particular embodiments. Further details of particular aspects of these techniques and devices are included in co-pending U.S. application Ser. No. 12/246,369 filed on Oct. 6, 2008 and incorporated herein by reference. Beginning with FIG. 3A, a practitioner passes a right atrial guidewire 250a into the right atrium 101 of the patient's heart 100. Optionally, the practitioner can continue to advance the right atrial guidewire 250a into the superior vena cava. The practitioner then passes a left atrial guidewire 250b into the right atrium 101, through the PFO tunnel 112 and into the left atrium 102. Accordingly, the left atrial guidewire 250b is positioned in the tunnel 112 between the primum 107 and the secundum 108. Suitable imaging processes (e.g., transthoracic ultrasound or TTE, intra-cardiac echo or ICE, transesophageal echo or TEE, fluoroscopy, and/or others) known to those of ordinary skill in the relevant art may be used to position the guidewires 250a, 250b and/or other devices used during the procedure. The guidewires 250a, 250b can then be used to guide one or more surgical tools into position. The tools may include one or more catheters, and/or other devices carried by the catheters.

In another embodiment, the left atrial guidewire 250b is routed as described above, but before the right atrial guidewire 250a is introduced. The right atrial guidewire 250a is instead pre-loaded into a delivery catheter (described later with reference to FIG. 3C), and the delivery catheter, with the right atrial guidewire 250a on board, is threaded along the left atrial guidewire 250b to the right atrium 101 (e.g., at or near the junction between the right atrium 101 and the inferior vena cava). Once the delivery catheter is in the right atrium 101, the right atrial guidewire 250a can be deployed to the location shown in FIG. 3A.

Figure 3B:
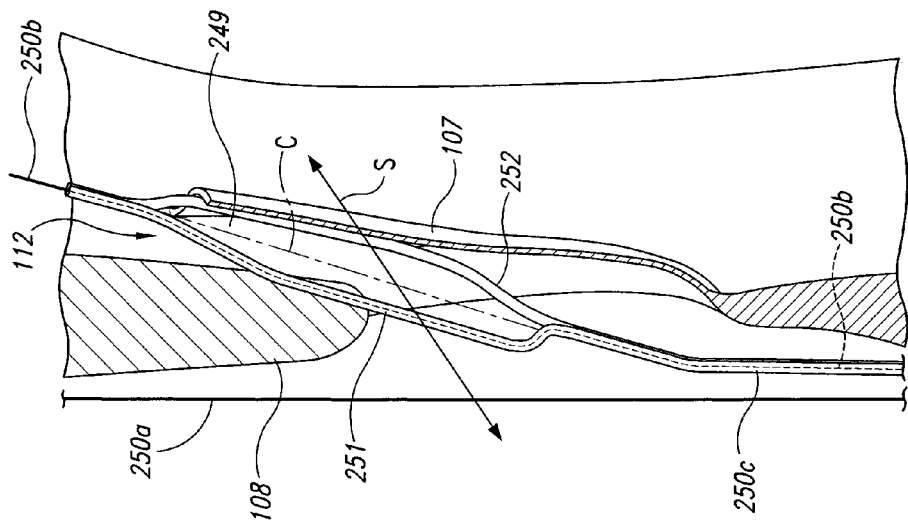
Figure 3A:
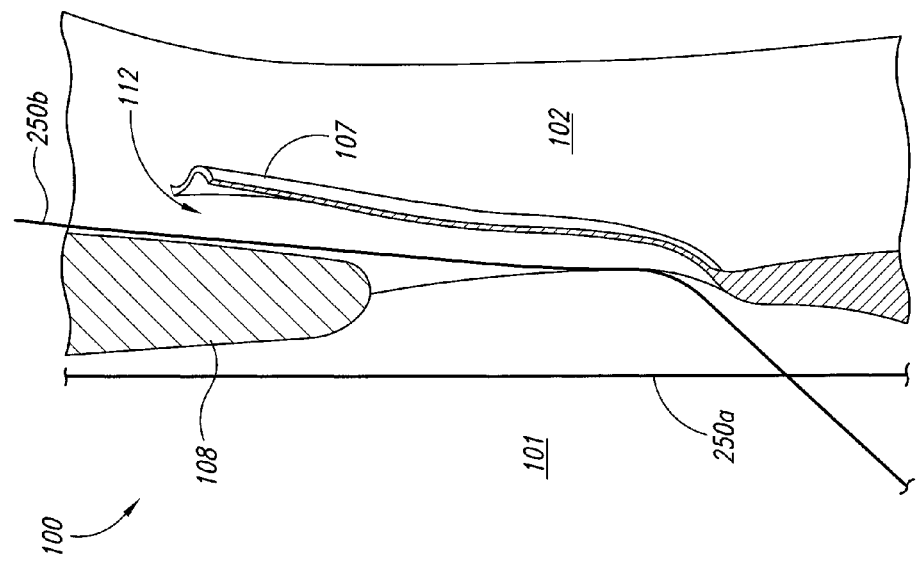

In FIG. 3B, the practitioner has threaded a self-centering guidewire 250c along the left atrial guidewire 250b and into the tunnel 112. Alternatively, the self-centering guidewire 250c can be pre-loaded into the delivery catheter (described later with reference to FIG. 3C) and both can be advanced together along the left atrial guidewire 250b. This latter arrangement, e.g., in combination with pre-loading the right atrial guidewire 250a as described above, can prevent the left atrial guidewire 250b and the right atrial guidewire 250a from becoming twisted. In either embodiment, the self-centering guidewire 250c can include a first branch 251 and a second branch 252 positioned around an enclosed region 249. In a particular aspect of this embodiment, the first branch 251 is hollow so as to receive the left atrial guidewire 250b along which the self-centering guidewire 250c is passed. The first and second branches 251, 252 can be at least somewhat compliant and resilient and can accordingly spread or tighten the primum 107 laterally, as indicated by arrow S, upon being introduced into the tunnel 112. By stretching the primum 107, the self-centering guidewire 250c can draw the primum 107 toward the secundum 108. In addition, the branches 251, 252 can be symmetric relative to a central axis C and can accordingly center the self-centering guidewire 250c within the PFO tunnel 112. Furthermore, the closed shape provided by the first and second branches 251, 252 can provide the guidewire 250c with a degree of lateral rigidity along the axis identified by arrow S. Accordingly, when the guidewire 250c is placed in the tunnel 112, the resilience provided by the primum 107 and/or the secundum 108 can force the guidewire 250c to assume the orientation shown in FIG. 3B, e.g., with the generally flat plane of the enclosed region 249 "sandwiched" between and facing toward the primum 107 on one side and the secundum 108 on the other. The lateral rigidity of the self-centering guidewire 250c when it is deployed can also prevent it from twisting, which in turn can make it easier for the practitioner to accurately seal the tunnel 112.

Figure 3D:
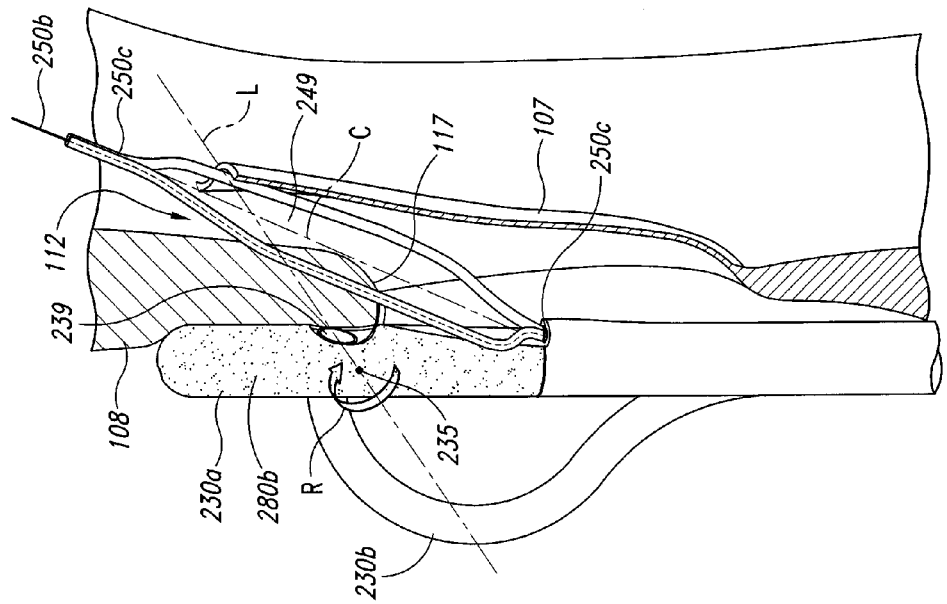
Figure 3C:
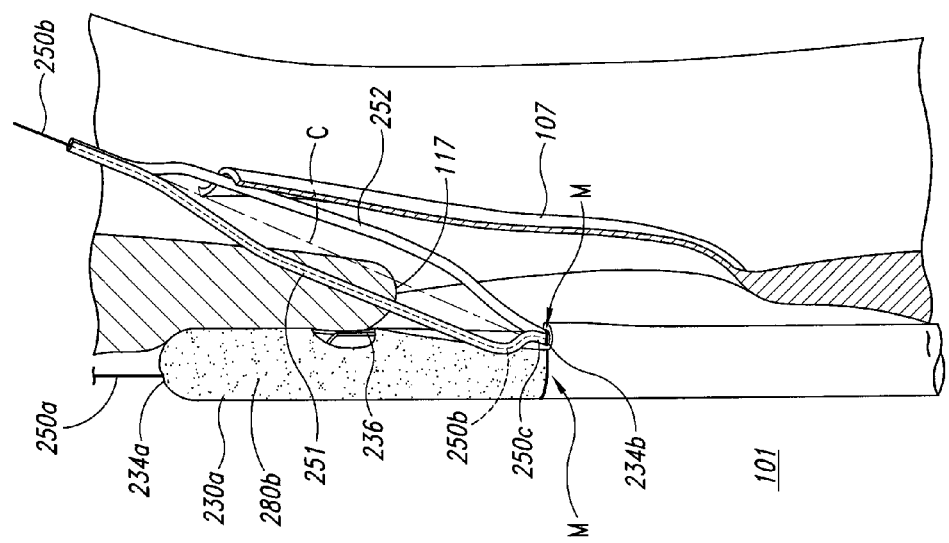

Turning next to FIG. 3C, the practitioner has threaded a delivery catheter 230a along the right atrial guidewire 250a and the self-centering guidewire 250c, which is in turn threaded along the left atrial guidewire 250b, as discussed above. Or, as discussed above, the right atrial guidewire 250a and the self-centering guidewire 250c can be pre-loaded into the delivery catheter 230a and deployed once the delivery catheter 230a has been threaded along the left atrial guidewire 250b until it is positioned in the right atrium 101. In either embodiment, the delivery catheter 230a can include a right atrial guidewire opening 234a that receives the right atrial guidewire 250a, and a left atrial guidewire opening 234b that receives the self-centering guidewire 250c and the left atrial guidewire 250b over which the self-centering guidewire 250c is passed. In this embodiment, the self-centering guidewire 250c has a generally elliptical cross-sectional shape, and accordingly, the left atrial guidewire opening 234b has a similar shape. With this arrangement, the self-centering guidewire 250c is "keyed" to the delivery catheter 230a. Accordingly, the delivery catheter 230a has a known orientation relative to the self-centering guidewire 250c when the delivery catheter 230a reaches the position shown in FIG. 3C. The upward progress of the delivery catheter 230a can be limited by a "tree crotch effect" provided by the delivery catheter 230a positioned on one side of the septal limbus 117, and the combined left atrial guidewire 250b and self-centering guidewire 250c on the other side of the limbus 117. In addition, radiopaque markers M (e.g., bands) can be located at the left atrial guidewire opening 234b and the point at which the branches 251, 252 bifurcate. In a particular embodiment, the markers M can therefore be co-located or nearly co-located when the delivery catheter 230a has been properly advanced. Once the delivery catheter 230a has the position shown in FIG. 3C, the right atrial guidewire 250a can optionally be withdrawn, or it can remain in place for additional steps, including for the remainder of the procedure.

As noted above with reference to FIG. 2, the overall system can include a return electrode positioned close to the PFO. FIG. 3C illustrates a return electrode 280b carried by the delivery catheter 230a so as to operate in a bipolar manner with an electrode delivered in accordance with an embodiment of the disclosure. In a particular aspect of this embodiment, the return electrode 280b can include an electrically conductive coating or sleeve positioned at the outside of the delivery catheter 230a, and coupled to an electrical return terminal (e.g., at the controller 221 shown in FIG. 2) via a lead wire (not visible in FIG. 3C). In another embodiment, the return electrode 280b can have other arrangements and/or configurations in which it is positioned close to the primum 107 and/or the secundum 108.

In FIG. 3D, a positioning catheter 230b (which is housed within and movable relative to the delivery catheter 230a) is deployed from the delivery catheter 230a. In this embodiment, the positioning catheter 230b is deployed by applying an axial force to it, causing it to buckle or bend outwardly through a corresponding slot (not visible in FIG. 3D) in the outer surface of the delivery catheter 230a. Accordingly, the positioning catheter 230b can assume the shape shown in FIG. 3D. In one arrangement, the distal end of the positioning catheter 230b is eccentrically connected to a pivot axle 235, which allows the positioning catheter 230b to rotate as indicated by arrow R as it buckles. As the positioning catheter 230b rotates, it can position the exit opening of a lumen 239 to face outwardly from the delivery catheter 230a.

The lumen 239 can also face directly toward the secundum 108, and can be aligned with the central axis C above the limbus 117, as a result of the features of the self-centering guidewire 250c, the delivery catheter 230a and the positioning catheter 230b. In particular, the self-centering guidewire 250c can be centered within the tunnel 112, with the plane defined by the enclosed region 249 facing directly toward the secundum 108.

As shown in FIG. 3E, a penetrating guidewire 260 can be deployed from the positioning catheter 230b. The penetrating guidewire 260 can include a penetrating member 261 that penetrates through the secundum 108 and the primum 107, so as to cross the entire septum 106 into the left atrium 102. In a particular embodiment, the penetrating member 261 can include an RF electrode that is advanced through the septum 106. The penetrating guidewire 260 can be operated in a bipolar manner, as indicated by field lines F. In particular, electrical power can be provided to the penetrating member 261, and the return electrode 280b can operate as a return path for electrical current provided to the penetrating member 261. In other embodiments, the penetrating guidewire 260 can use other return electrodes. Further details of penetrating guidewires and associated systems are described later with reference to FIGS. 4-9.

In FIG. 3F, the practitioner advances an electrode catheter 230c along the penetrating guidewire 260 from the right atrium 101 into the left atrium 102. The electrode catheter 230c can include a dilator 237 that temporarily stretches the opening initially created by the penetrating guidewire 260 to allow additional components to pass into the left atrium 102. These components can include an inflatable member 290 (shown collapsed) and an electrode device 280. In a particular embodiment, the penetrating guidewire 260 can form a hole having a diameter of about one millimeter, and the dilator 237 can have a diameter of about two millimeters to temporarily stretch the hole to a diameter of about two millimeters. When the electrode catheter 230c and the penetrating guidewire 260 are later withdrawn, the hole can relax back to a diameter of about one millimeter. In other embodiments, these dimensions can have other values. In any of these embodiments, the dilator 237 and/or the penetrating member 261 can include radiopaque markings for enhanced visibility during fluoroscopic visualization.

Figure 3G:
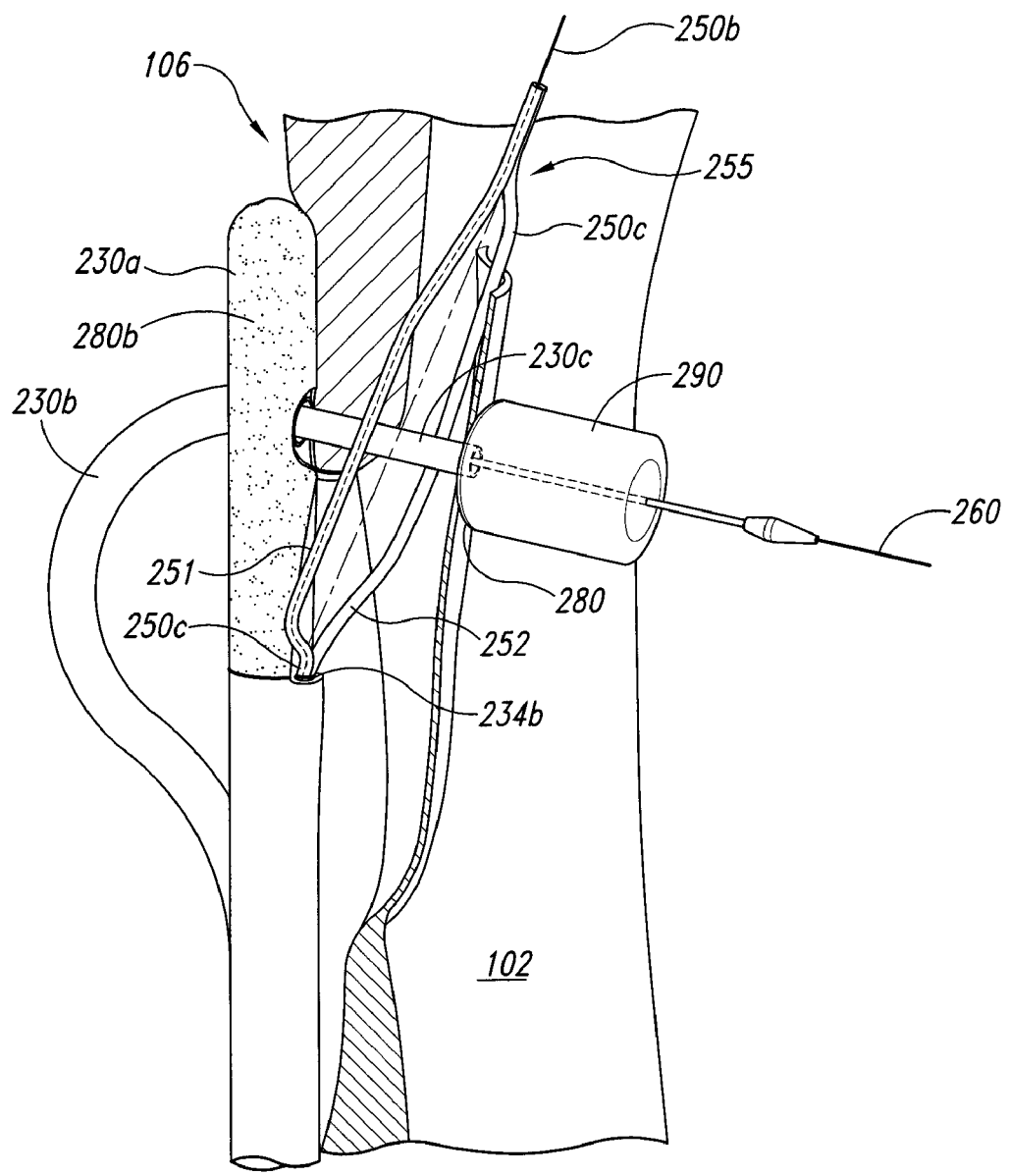

In FIG. 3G, the practitioner has inflated the inflatable member 290 (e.g., with saline or another suitable inflation medium) in the left atrium 102, and has also deployed the electrode device 280. In a particular embodiment, the electrode device 280 includes a conductive coating applied to a proximally facing surface of the inflatable member 290. The inflatable member 290 can be formed from a non-stretch material so that it maintains a predefined shape (e.g., the cylindrical shape shown in FIG. 3G) when inflated. This arrangement can also prevent or restrict the conductive coating from delaminating, flaking, and/or otherwise detaching from the inflatable member 290. Other suitable electrode shapes and configurations are described later with reference to FIG. 9 and in pending U.S. application Ser. No. 12/246, 369, previously incorporated herein by reference. In at least some of these embodiments, the inflatable member 290 is eliminated.

Prior to engaging the electrode device 280 with the septum 106, the practitioner can withdraw the self-centering guidewire 250c and the left atrial guidewire 250b by separating or opening the first and second branches 251, 252 at a separation location 255, allowing them to pass downwardly around opposite sides of the electrode catheter 230c and into the left atrial guidewire opening 234b. Further details of embodiments for performing this task are described in U.S. application Ser. No. 12/246,369, previously incorporated by reference.

Figure 3I:
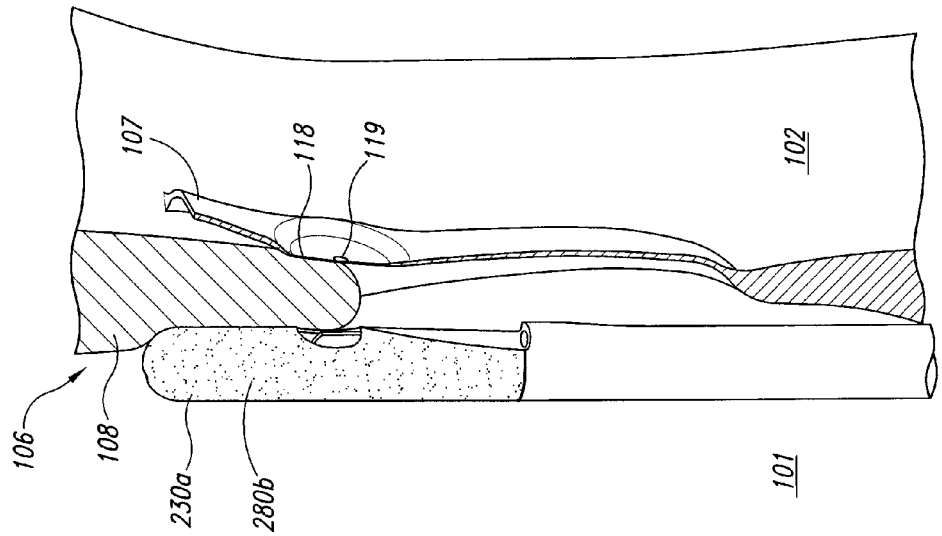
Figure 3H:
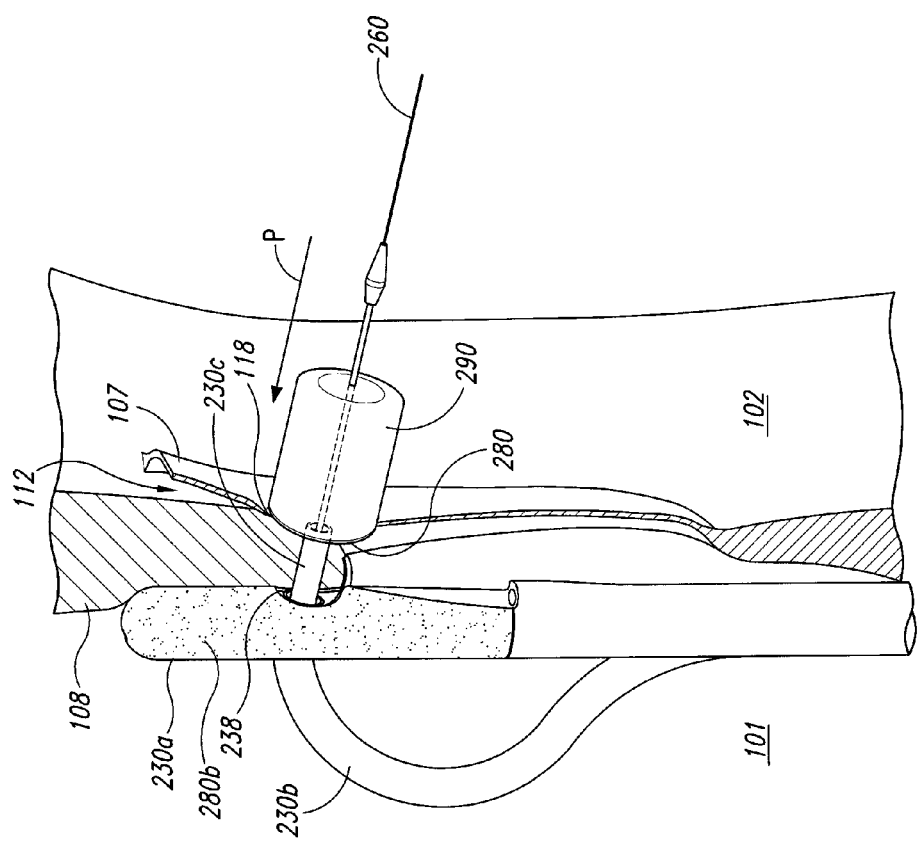

In FIG. 3H, the self-centering guidewire 250c (FIG. 3G) and the left atrial guidewire 250b (FIG. 3G) have been removed, and the practitioner has applied an axial force to the electrode catheter 230c in a generally proximal direction P. The axial force draws the inflatable member 290 and the electrode device 280 snugly up against the primum 107. This force can also clamp the primum 107 against the secundum 108, and can clamp both the primum 107 and the secundum 108 between the electrode device 280 and a backstop surface 238. In an embodiment shown in FIG. 3H, the backstop surface 238 includes the outwardly facing, conductive external surface of the delivery catheter 230a, e.g., the return electrode 280b. Accordingly, the electrode device 280 can operate in a bipolar manner via the return electrode 280b. In other embodiments, the backstop surface 238 can have other locations and/or arrangements. For example, the backstop surface 238 can be separate from the delivery catheter 230a, and/or can be electrically non-conductive, so that the electrode device 280 operates in a monopolar manner, e.g., via the remote return electrode 280a shown in FIG. 2.

With the electrode device 280 in the position shown in FIG. 3H, the practitioner can apply electrical energy (e.g., a varying electrical current) to the electrode device 280. RF energy provided to the electrode device 280 is received by the adjacent tissue so as to heat both the primum 107 and the secundum 108. The heat can at least partially fuse, glue, cement, or otherwise seal, join or connect the primum 107 and the secundum 108 together, forming a seal 118 that partially or completely closes the PFO tunnel 112 between the left atrium 102 and the right atrium 101.

After the tissue fusing and/or sealing process has been completed, the inflatable member 290 can be collapsed and the electrode catheter 230c, the positioning catheter 230b and the penetrating guidewire 260 can be withdrawn into the delivery catheter 230a, as is shown in FIG. 3I. A residual opening 119 may remain in the seal 118 as a result of withdrawing the electrode catheter 230c and penetrating guidewire 260 (FIG. 3H) back through the septum 106 from the left atrium 102 to the right atrium 101. The residual opening 119 is typically very small (e.g., on the order of one millimeter) and is expected to close quickly as a result of the body's normal healing process. The practitioner then withdraws the delivery catheter 230a from the patient's body. In other cases in which the seal 118 may initially be incomplete for other reasons, it is also expected that the seal will be sufficient to allow the body's normal healing processes to complete the closure, generally in a short period of time.

C. Penetrating Guidewires and Associated Systems and Methods

FIGS. 4-9 illustrate further details of penetrating guidewires configured in accordance with particular aspects of the present disclosure. These guidewires can be used to penetrate the interatrial septum 106 as described above with reference to FIG. 3E. In other embodiments, these guidewires can be used to penetrate other tissues.

FIG. 4 is a partially schematic, isometric illustration of the guidewire 260 carrying a penetrating member 261 configured in accordance with an embodiment of the disclosure. The penetrating guidewire 260 can include a wire 262 or other electrically conductive, flexible element that is elongated along an elongation axis 271 to include a distal portion 277 and a proximal portion 278. The wire 262 can be formed from a suitable conductive material, e.g. superelastic nitinol, and can have a coating 263 formed from a material that electrically insulates the wire 262, and can facilitate the movement of components sliding along the penetrating guidewire 260. For example, the coating 263 can include Teflon® or another suitable material. The underlying wire 262 can include compositions and/or coatings (e.g. a gold plating) that facilitate visualizing the wire 262 via fluoroscopy or other existing visualization techniques.

The penetrating member 261 is located at a distal region of the wire 262, with the distal and proximal directions indicated by arrows D and P, respectively. In an embodiment shown in FIG. 4, the penetrating member 261 has geometric features that are configured to enhance the ability of the penetrating member 261 to penetrate through septal tissue, while conserving the electrical power consumed by the penetrating member 261 as it does so, and/or while reducing the likelihood that the penetrating member 261 will cause blood clotting once it has penetrated through the septum. The penetrating member 261 can also include features that reduce or eliminate the likelihood for the penetrating guidewire 261 to penetrate into tissue in an unplanned manner. Further details of these features are described below.

In a particular aspect of an embodiment shown in FIG. 4, the penetrating member 261 includes multiple blade segments, collectively referred to as blade segments 264, and identified individually in FIG. 4 as first, second, third, and fourth blade segments 264a, 264b, 264c, 264d, respectively. Individual blade segments 264 can be orthogonal to each other, and can extend axially along the elongation axis 271 to include a first or distal region 270a, and a second or proximal region 270b. Individual blade segments 264 also extend radially outwardly from the elongation axis 271, e.g., from a blade root 269 to an outer peripheral surface 265. The blade segments 264 can accordingly include a first sidewall 266a and an oppositely facing second sidewall 266b. In an embodiment shown in FIG. 4, the sidewalls 266a, 266b are generally flat, and in other embodiments, the sidewalls 266a, 266b can have contoured or otherwise curved shapes. In at least some embodiments, the overall appearance of the penetrating member 261 can be somewhat similar to the end of a Phillips head screwdriver.

The individual blade segments 264 can taper in one or more of several directions. For example, as shown in FIG. 4, the outer peripheral surface 265 of the blade segments 264 can taper away from the elongation axis 271 in the proximal direction P in the first region 270a. The outer peripheral surfaces 265 of the blade segments 264 can then taper inwardly toward the elongation axis 271 in the proximal direction P in the second region 270b. This tapered shape can facilitate gradually increasing the effective diameter of the opening made by the penetrating member 261 as it is energized and moved through the septal tissue. The tapered shape can define an elliptical profile, e.g., a circular profile, as shown in FIG. 4. Accordingly, the overall envelope formed by the outer peripheral surfaces 265 can be ellipsoidal (e.g., spherical). In other embodiments, the tapered shape can define other rounded profiles, and in still further embodiments, the profiles can include straight segments.

The blade segments 264 can taper in other directions in addition to or in lieu of tapering in the directions described above. For example, a blade width W at the root 269 of the blade segments 264 can decrease in the distal direction D, as indicated by the first blade segment 264a shown in FIG. 4. In addition, the width W of the blade segments 264 can decrease in the radial direction R, outwardly from the elongation axis 271 to the outer peripheral surface 265.

The distal ends of each of the blade segments 264 can meet to form a generally blunt tip 268 at a distal surface 272 of the penetrating member 261. For example, the outer peripheral surfaces 265 of the blade segments 264 can include sections of an elliptical or a spherical surface, which form the outwardly tapering contour in the first region 270a, the inwardly tapering contour in the second region 270b, and the generally blunt tip 268. The proximal ends of the blade segments 264 can meet at a proximal surface 273 of the penetrating member 261. The penetrating guidewire 260 can include a thermal insulator 275 at the proximal surface 273. The thermal insulator 275 can shield the dilator 237 (FIG. 3F) from heat resulting from activation of the penetrating member 261. The proximal surface 273 of the penetrating member 261 can have a radial extent that matches or approximately matches the radial extent of the insulator 275, so as to eliminate any proximally or distally facing steps at this interface, which might interfere with the process of advancing and retracting the guidewire 260.

The foregoing features may be formed in the penetrating member 261 using any of a variety of suitable manufacturing techniques. For example, one suitable technique includes integrally forming the wire 262 with the penetrating member 261 by melting a distal end of the wire 262 to form a solid spherical element. If the volume of material at the distal end of the wire 262 is not sufficient to form the penetrating member 261, it can be supplemented with additional material, e.g., in the form of the small tube. The manufacturer can then remove material from the spherical element to form the blade segments 264. This material can be removed using Electrical Discharge Machining (EDM) and/or other suitable techniques, e.g., grinding or other machining processes. In still further embodiments, the penetrating member 261 can be molded or otherwise formed without removing material or using other subtractive techniques. In a particular embodiment, the overall diameter of the penetrating member 261 can be in the range of from about 0.030 inch to about 0.060 inch (e.g., about 0.050 inch). The particular value selected for the diameter can depend on the particular use to which the penetrating member 261 is put, the patient's anatomy, and/or the size of the device to be passed along the guidewire 260. When used for a transseptal puncture and PFO sealing process as described above with reference to FIGS. 3A-3I, it is generally desirable to size the penetrating member 261 so as to make the transseptal puncture large enough that the electrode catheter 230c (FIG. 3F) will not buckle and damage adjacent tissue when the dilator 237 (FIG. 3F) is pushed through the opening, yet not so large as to significantly extend the period of time required to heal the residual opening 119 (FIG. 3I).

In a particular embodiment, power can be supplied to the penetrating guidewire 260 at from about 150 $V_{rms}$ to about 250 $V_{rms}$ (e.g., about 200 $V_{rms}$ or about 225 $V_{rms}$) and a frequency of from about 100 KHz to about 5 MHz (e.g., about 480 KHz). The power can be applied for about 2 seconds continuously in one embodiment, and in another embodiment, the power can be applied over a time period that ranges from about 1 second to about 5 seconds. In still further embodiments, the power can be applied for time periods of less than 1 second, for example, from about 0.01 seconds to about 0.1 seconds.

FIG. 5 is an enlarged, isometric illustration of the penetrating member 261 shown in FIG. 4. FIG. 5 further illustrates the generally blunt (e.g. spherical) tip 268 of the penetrating member 261. FIG. 5 also illustrates the generally sharp edges between the outer peripheral surface and the associated sidewalls. For example, FIG. 5 illustrates the first and second sidewalls 266a, 266b of the first blade segment 264a, and the intersections between these sidewalls and the outer peripheral surface 265. The intersections form first and second edges 267a, 267b, which can be generally sharp, despite the relatively gentle curvature of the outer peripheral surface 265. In particular embodiments, the radii of curvature at the intersections between the first and second edges 267a, 267b and the outer peripheral surface 265 can be less than about 0.001 inch and in further particular embodiments, less than about 0.0005 inch.

One feature of the generally sharp edges 267a, 267b shown in FIG. 5 is that they can produce a more concentrated or intense electric field when high frequency electrical energy is applied to the penetrating member 261 than can a uniformly spherical surface. Accordingly, the penetrating member 261 can more easily penetrate through the septal tissue, as described above with reference to FIG. 3E. For example, the practitioner can penetrate through the septal tissue without having to provide an undue amount of axial force on the penetrating guidewire 260. This arrangement can reduce the time it takes to move the penetrating member 261 and the penetrating guidewire 260 through the septal tissue and/or ease the practitioner's task.

Another feature of embodiments of the penetrating member 261 described above is that the edges 267a, 267b can form well-defined slits in the septal tissue. When the dilator 237 passes through the opening formed by the slits, the slits can extend radially outwardly, also in a well-defined manner, to form small tissue flaps. Accordingly, the size and shape of the dilated opening can be more uniform and controlled than an opening formed by a blunt electrode. The small, uniform tissue flaps can also heal more readily than can openings with jagged or otherwise irregular edges.

Still another feature of embodiments of the penetrating member 261 is that the sharp edges 267a, 267b can facilitate sparking at a lower applied voltage than can a relatively blunt sphere. Rapid sparking action is the expected mechanism by which the adjacent tissue is rapidly heated and volatilized, creating cavities that form the tissue slits described above. By reducing the voltage applied to the penetrating member, the practitioner's control over the opening formed in the tissue can be improved, and the likelihood for creating unnecessary tissue trauma can be reduced.

Another aspect of embodiments of the penetrating member 261 is that the device designer and/or manufacture can establish the parameters in accordance with which power is applied to the penetrating member 261 in a manner that (a) facilitates sparking and the associated tissue erosion in the septal tissue, and (b) results in no sparking once the penetrating member 261 passes from the tissue into the adjacent blood field in the left atrium. For example, the designer/manufacturer can select the voltage applied to penetrating member 261 to be (a) high enough to create sparks when the penetrating member 261 is in contact with the septal tissue (which has a first impedance), and (b) low enough so that if power is still applied to the penetrating member 261 when it contacts the blood field (which has a second impedance less than the first), no sparks are formed. This feature is advantageous because avoiding sparks in the blood field reduces the likelihood for forming clots. The designer/manufacturer can achieve this result by establishing a maximum voltage applied to the tissue penetrating member 261 and/or by establishing other parameters, including the internal impedance of the power source included in the system controller 221 (FIG. 2). This approach can be used for penetrating members having a wide variety of geometries, including, but not limited to those disclosed herein. Such penetrating member may be used in contexts of other atrial septal penetration for PFO closure, e.g., other contexts in which the penetrating member emerges from a relatively high impedance tissue into a relatively low impedance liquid.

Another feature of an embodiment of the penetrating member 261 shown in FIGS. 4 and 5 is that the tip 268 is relatively blunt, despite the sharp edges 267a, 267b of the sidewalls 266a, 266b. This configuration is expected to reduce or eliminate the likelihood that the penetrating member 261 will inadvertently damage the left atrial tissue once the guidewire 260 emerges into the left atrium. In particular, the penetrating member 261 is expected to include enough edges with sufficient sharpness to produce concentrated electric fields (and associated efficient cutting forces) when activated with RF energy, and yet be blunt enough to avoid inadvertently penetrating cardiac tissue. For example, if the tip 268 inadvertently comes into contact with cardiac tissue in the left atrium after the penetrating operation has been completed and the high frequency energy applied to the penetrating member 261 is halted, the bluntness of the tip 268 can prevent it from penetrating into the left atrial tissue.

As shown in FIGS. 4 and 5, the penetrating member 261 can have generally spherical outer peripheral surfaces 265, and a generally spherical distal surface 272. In other embodiments, the outer peripheral surfaces 265 and/or distal surfaces 272 can have other generally curved surfaces that provide generally sharp edges for the blade segments, and that also provide a generally blunt or otherwise atraumatic tip 268. For example, FIG. 6 illustrates a penetrating member 661 having generally ellipsoidally shaped outer peripheral surfaces 665. The aspect ratio of the ellipsoid that forms the outer peripheral surfaces 665 can be greater than one (as shown in FIG. 6) or less than one. When the aspect ratio of the ellipsoid is equal to one, the ellipsoid has a generally spheroidal shape, as shown in FIGS. 4 and 5.

In further embodiments, the penetrating member can have other shapes that produce at least some of the effects described above with reference to the embodiments shown in FIGS. 4-6. For example, FIG. 7 illustrates a penetrating member 761 having blade segments 764a-764d with roots 769 that are generally parallel to the elongation axis 271. Accordingly, the individual blade segments 764 taper in a radially outward direction between the root 769 and the corresponding outer peripheral surface 765, but have a generally fixed width W along the length of the root 769.

Figure 8A:
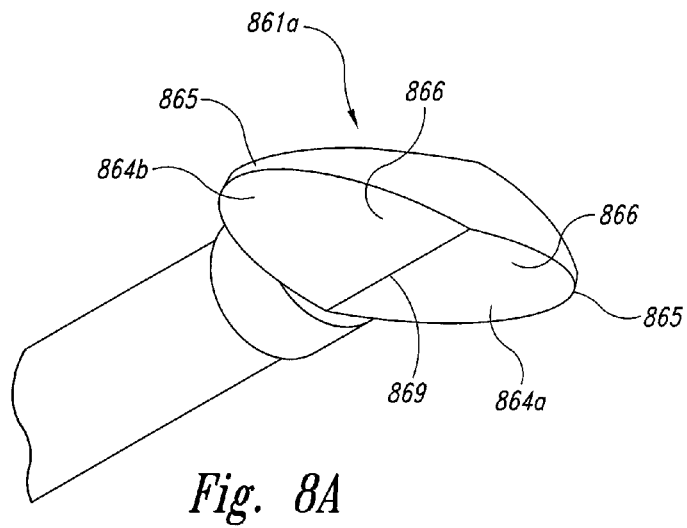
FIG. 8A is a partially schematic, side view of a guidewire having a penetrating member with two blade segments configured in accordance with still another embodiment of the disclosure.
Figure 8B:
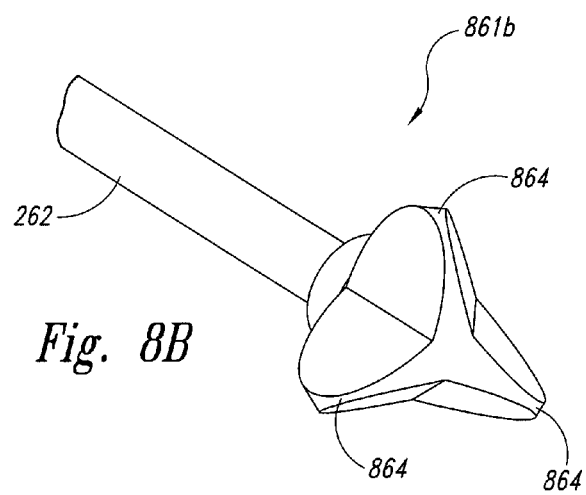
FIG. 8B is a partially schematic illustration of a guidewire having a penetrating member with three blade segments configured in accordance with yet another embodiment of the disclosure.

FIG. 8A is a partially schematic, isometric illustration of a penetrating member 861a having two blade segments 864, shown as a first blade segment 864a and a second blade segment 864b. The blade segments 864 include sidewall surfaces 866 that can be flat and can extend from a corresponding root 869 to a corresponding outer peripheral surface 865. The blade segments 864 can be distinct, e.g., with a distinct root 869 and distinct sidewall surfaces 866, or the blade segments 864 can blend to form a single, unitary blade segment. In at least some embodiments, the arrangement shown in FIG. 8a may be simpler to manufacture than the arrangements shown in FIGS. 4-7, while still producing a transseptal puncture that is sized and shaped in a manner suitable for transseptal delivery of additional system elements (e.g., the electrode 280 shown in FIG. 3H. Conversely, it is expected that the four blade segment arrangement shown in FIGS. 4-7 will produce a more controlled transseptal puncture in at least some clinical settings. For example, it is expected that the four blade segment arrangement may be less likely to deviate from a straight-line path through the septal tissue. FIG. 8B illustrates a penetrating member 861b having three blade segments 864 spaced apart circumferentially by approximately 120° in accordance with still another embodiment of the disclosure. Other aspects of the penetrating member 861b (e.g., the blade edge) can be generally similar to those described above with reference to FIGS. 4-7. Like the four blade segment arrangement, this arrangement is expected to resist deviations from a straight-line path through the septal tissue.

Figure 9:
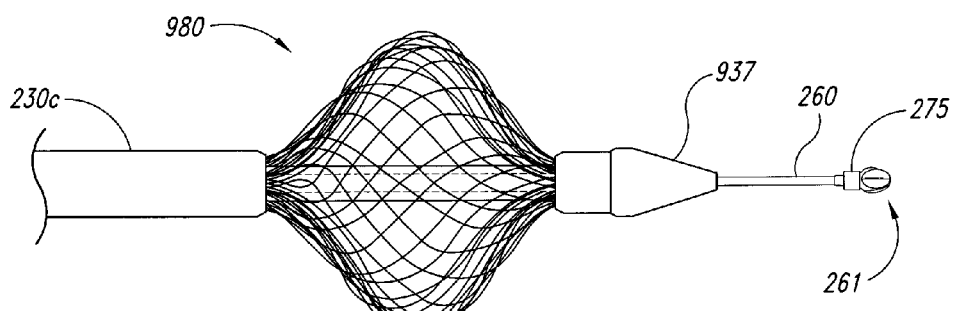
FIG. 9 is a partially schematic illustration of a guidewire along which a catheter carrying an electrode in accordance with another embodiment of the disclosure is threaded.

FIG. 9 is a partially schematic, isometric illustration of an overall system that includes the guidewire 260, the penetrating member 261, the insulator 275, and other features suitable for penetrating through a patient's cardiac septum in accordance with an embodiment of the disclosure. For example, the overall system can include one or more tools and/or patient treatment devices that are threaded along the guidewire 260. One such device is a dilator 937 similar in at least some respects to that discussed above with reference to FIG. 3F. Other tools/devices include an electrode 980 formed from braided elements so as to be changeable between an expanded configuration (shown in FIG. 9) and a collapsed configuration. This electrode arrangement can replace the electrode 280 and the inflatable device 290 described above with reference to FIGS. 3F-3G. Further details of embodiments including electrodes having generally similar configurations are disclosed in pending U.S. application Ser. No. 12/246,369, previously incorporated by reference. In some embodiments, the guidewire 260 can slideably support electrodes having other configurations, and/or it can support other patient treatment devices.

From the foregoing, it will be appreciated that specific embodiments have been described herein for purposes of illustration, but that various modifications may be made without deviating from the present disclosure. For example, the penetrating members can have shapes other than those expressly shown in the Figures. In a particular embodiment, the penetrating members can have three blade segments and in other embodiments, the penetrating members can have more than four blade segments (e.g., five blade segments). In other embodiments, the penetrating member can have a plurality of outwardly projecting spikes that provide a concentrated electrical field for cutting through the septal tissue. The ends of the spikes can be flattened or otherwise blunted to reduce the likelihood for penetration into left atrial tissue, other than the atrial septum.

Certain aspects of the disclosure described in the context of particular embodiments may be combined or eliminated in other embodiments. For example, embodiments of the penetrating guidewire may be used without the self-centering guidewire or the tissue sealing electrode described above. In particular embodiments, the penetrating guidewire may be used for procedures that do not include PFO sealing, or procedures that do not include cardiac tissue. Further, while advantages associated with certain embodiments have been described in the context of those embodiments, other embodiments may also exhibit such advantages, and not all embodiments need necessarily exhibit such advantages to fall within the scope of the present disclosure. Accordingly, the disclosure can include other embodiments not expressly shown or described above.

We claim:

1. A patient treatment system, comprising:
   a tissue-penetrating guidewire, including:
   an elongated flexible segment having a distal portion and a proximal portion;
   a penetrating member at the distal portion, the penetrating member including four orthogonally-oriented blade segments, each blade segment having a generally ellipsoidal outer peripheral surface and first and second oppositely-facing sidewalls extending inwardly from the outer peripheral surface to a blade root, with a width of each blade segment between the oppositely-facing sidewalls at the blade root that narrows in a distal direction, the four blade segments meeting at a distal end of the penetrating member to form a blunt, generally ellipsoidal tip, each blade segment having a first generally sharp edge between the first sidewall and the outer peripheral surface and a second generally sharp edge between the second sidewall and the outer peripheral surface;
   an electrical current source electrically connected to the flexible segment to deliver RF current to the penetrating member; and
   a patient treatment device slideably positioned along the guidewire.

2. The system of claim 1 wherein the penetrating member has a generally spherical tip, and wherein each blade segment has a generally spherical outer peripheral surface.

3. The system of claim 1 wherein the width of each blade segment narrows in a radially outward direction as well as in the distal direction.

4. The system of claim 1 wherein the patient treatment device includes a catheter having a lumen in which the guidewire is slideably received, and a tissue-sealing electrode carried by the catheter and slideable relative to the catheter along the guidewire.

5. The system of claim 1 wherein the penetrating member includes a distal surface and a proximal surface and wherein the system further comprises an insulator positioned along the flexible segment adjacent to the proximal surface of the penetrating member.

6. The system of claim 1 wherein the patient treatment device includes a tissue dilator positioned along the tissue penetrating guidewire, the tissue dilator having a radial dimension that increases in a proximal direction.

7. The system of claim 6, wherein the penetrating member includes a distal surface and a proximal surface and wherein the system further comprises a thermal insulator positioned along the flexible segment between the penetrating member and the tissue dilator.

8. The system of claim 7 wherein the insulator has a radial extent that is approximately equal to a radial extent of the proximal surface of the penetrating member.

9. The system of claim 1 wherein each of the first and second generally sharp edges have a radius of 0.0005 inch or less.

10. A patient treatment system, comprising:
    a tissue-penetrating guidewire that includes:
    a flexible segment having a distal portion and a proximal portion, the flexible segment being elongated along an elongation axis, the proximal portion being coupleable to an electrical current source and shaped to receive a patient treatment device from a proximal-most end for slideable movement along an outer portion of the flexible segment toward the distal portion; and
    a penetrating member at the distal portion, the penetrating member including at least one blade segment having a tapered outer peripheral surface and an adjacent generally sharp edge, the blade segment extending to a distal end of the penetrating member to form a generally blunt tip.

11. The system of claim 10 wherein the penetrating member includes two blade segments positioned 180° apart from each other.

12. The system of claim 10 wherein the penetrating member includes three blade segments positioned 120° apart from each other.

13. The system of claim 10 wherein the penetrating member includes four blade segments positioned 90° apart from each other.

14. The system of claim 10 wherein the blade segment has generally oppositely facing blade surfaces that taper toward each other in a radially outward direction.

15. The system of claim 10 wherein the blade segment has generally oppositely facing blade surfaces that taper toward each other in a distal direction.

16. The system of claim 10 wherein the outer peripheral surface of the blade segment tapers outwardly away from the elongation axis in a proximal direction over a first region adjacent to the tip, and tapers inwardly toward the elongation axis in a proximal direction over a second region proximal to the first region.

17. The system of claim 10 wherein the outer peripheral surface has a generally ellipsoidal shape.

18. The system of claim 10 wherein the outer peripheral surface has a generally spherical shape.

19. The system of claim 10 wherein the blade segment has generally oppositely facing sidewall surfaces that form the generally sharp edge at an intersection with the tapered outer peripheral surface.

20. The system of claim 10, further comprising a tissue dilator positioned along the tissue penetrating guidewire, the tissue dilator having a radial dimension that increases in a proximal direction.

21. The system of claim 20, wherein the penetrating member includes a distal surface and a proximal surface and wherein the system further comprises a thermal insulator positioned along the tissue penetrating guidewire between the penetrating member and the tissue dilator.

22. The system of claim 10, further comprising a patient treatment device slideably positioned along the guidewire.

23. A method for treating a patient, comprising:
    introducing a guidewire into a patient's body;
    placing a penetrating member located at a distal end of the guidewire into contact with patient tissue, the penetrating member including at least one blade segment having a tapered outer peripheral surface and an adjacent generally sharp edge, the blade segment extending to a distal end of the penetrating member to form a blunt tip;
    applying RF electrical energy to the guidewire to form an opening in the tissue; and
    increasing a size of the opening by advancing the tapered outer peripheral surface of the penetrating member through the tissue.

24. The method of claim 23 wherein forming an opening in the tissue includes forming an opening extending through the atrial septum of a patient having a patent foramen ovale.

25. The method of claim 24, further comprising advancing an RF tissue sealing electrode along the guidewire and activating the tissue sealing electrode in the patient's left atrium to close the patient's patent foramen ovale.

26. The method of claim 23 wherein applying RF electrical energy includes forming an electrical field in a region adjacent to the generally sharp edge, the electrical field having a greater field strength at the edge than at the blunt tip.

27. The method of claim 23 wherein placing a penetrating member located at a distal end of the guidewire into contact with patient tissue includes simultaneously placing four blade segments of the penetrating member into contact with the patient tissue.

28. The method of claim 23 wherein placing a penetrating member located at a distal end of the guidewire into contact with patient tissue includes simultaneously placing three blade segments of the penetrating member into contact with the patient tissue.

29. A method for treating a patient, comprising:
introducing a guidewire into a patient's body;
placing a penetrating member located at a distal end of the guidewire into contact with the right side of the patient's atrial septum, the penetrating member including four blade segments, each blade segment having a generally ellipsoidal outer peripheral surface and first and second oppositely-facing sidewalls extending inwardly from the outer peripheral surface to a blade root, with a width of each blade segment between the oppositely-facing sidewalls at the blade root that narrows in a distal direction, the four blade segments meeting at a distal end of the penetrating member to form a blunt, generally ellipsoidal tip, each blade segment having a first generally sharp edge between the first sidewall and the outer peripheral surface and a second generally sharp edge between the second sidewall and the outer peripheral surface;
applying RF electrical energy to the guidewire to form an opening in the secundum and primum of the atrial septum;
increasing a size of the opening by advancing the outer peripheral surfaces of the penetrating member through atrial septum into the patient's left atrium;
advancing a tissue sealing electrode along the guidewire through the opening and into the patient's left atrium; and
sealing a patent foramen ovale in the patient's atrial septum by applying RF electrical energy to the tissue sealing electrode.

30. The method of claim 29 wherein applying RF electrical energy to the guidewire includes generating a stronger electrical field at the first and second generally sharp edges than at the blunt tip.

31. The method of claim 29, further comprising ceasing to apply the RF energy to the guidewire and advancing the tip into contact with the patient's left atrial wall, without penetrating into the left atrial wall.

32. The method of claim 29 wherein the penetrating member has an overall diameter, and wherein the method further comprises reducing a likelihood for left atrial blood to clot upon contact with the penetrating member, compared with the likelihood for clotting upon contact with a uniformly spherical penetrating member of the same overall diameter.

* * * * *